US008567392B2

(12) United States Patent
Rumph et al.

(10) Patent No.: US 8,567,392 B2
(45) Date of Patent: *Oct. 29, 2013

(54) ELECTRONIC ANESTHESIA DELIVERY APPARATUS

(75) Inventors: Brad Rumph, Vallonia, IN (US); Tom Hoehler, Louisville, KY (US); Mark Lerman, Pomona, NY (US)

(73) Assignee: Vetland Medical Sales and Services LLC, Louisville, KY (US)

( * ) Notice: Subject to any disclaimer, the term of this patent is extended or adjusted under 35 U.S.C. 154(b) by 525 days.

This patent is subject to a terminal disclaimer.

(21) Appl. No.: 12/900,111

(22) Filed: Oct. 7, 2010

(65) Prior Publication Data
US 2011/0056491 A1    Mar. 10, 2011

Related U.S. Application Data

(63) Continuation-in-part of application No. 11/031,661, filed on Jan. 7, 2005, now Pat. No. 7,836,882.

(51) Int. Cl.
*A61M 11/00* (2006.01)
(52) U.S. Cl.
USPC ............................... 128/203.12; 128/204.21
(58) Field of Classification Search
USPC ............. 128/203.12, 204.18–205.18, 203.14; 604/65, 890.1; 345/173
See application file for complete search history.

(56) References Cited

U.S. PATENT DOCUMENTS

| | | |
|---|---|---|
| 2,890,696 A | 6/1959 | Morris |
| 3,385,578 A | 5/1968 | Porter |
| 3,593,710 A | 7/1971 | Eichelman et al. |

(Continued)

OTHER PUBLICATIONS

The United States Patent and Trademark Office; The International Search Report and the Written Opinion of the International Searching Authority, or the Declaration; Oct. 17, 2007; pp. 1-8; The United States Patent and Trademark Office; USA.

*Primary Examiner* — Steven Douglas
(74) *Attorney, Agent, or Firm* — Middleton Reutlinger (57) ABSTRACT

An electronic anesthesia delivery apparatus for mixing a carrier gas and first and second anesthetic agents comprises a chassis having an electronic vaporizer, the vaporizer having a first anesthetic chamber and a second anesthetic chamber retaining the first anesthetic agent and the second anesthetic agent, a carrier gas input port in flow communication with the first anesthetic chamber and the second anesthetic chamber, a precision orifice and an electronic control valve corresponding to each of the chambers being downstream of the gas input port, each of the chambers having a conduit in flow communication with the carrier gas input port, each of the conduits extending into each of the chambers below an upper level of anesthetic agent, wherein the carrier gas passes through a porous diffuser near an end of the conduit and bubbles through the anesthetic agent, the chamber further comprising an anesthetic gas outlet port, an electronic touchscreen display for controlling carrier gas flow rate to the first anesthetic chamber and the second anesthetic chamber, the electronic touchscreen display further allowing control of concentrations of the anesthetic agent in an anesthesia to a patient by intermittently opening and closing of the electronic control valve, a circuit board having an input/output portion, the circuit board in electronic communication with the electronic touchscreen display, the input/output portion receiving temperature of the anesthetic agent, the electronic anesthesia delivery apparatus allowing use of a first anesthetic agent while a second anesthetic agent is one of either replaced or substituted in the second chamber.

19 Claims, 8 Drawing Sheets

(56) References Cited

U.S. PATENT DOCUMENTS

| | | |
|---|---|---|
| 3,703,172 A | 11/1972 | Hay |
| 3,838,687 A | 10/1974 | Mosher |
| 3,869,771 A | 3/1975 | Bollinger |
| 4,276,243 A | 6/1981 | Partus |
| 4,436,674 A | 3/1984 | McMenamin |
| 4,750,483 A | 6/1988 | Ankartross et al. |
| 4,770,168 A | 9/1988 | Rusz et al. |
| 4,807,615 A | 2/1989 | Nakagawa et al. |
| 5,237,990 A | 8/1993 | Psaros et al. |
| 5,718,223 A | 2/1998 | Protas et al. |
| 5,730,119 A | 3/1998 | Lekholm |
| 5,806,513 A | 9/1998 | Tham et al. |
| 5,918,595 A | 7/1999 | Olsson et al. |
| 6,143,181 A | 11/2000 | Falkvall et al. |
| 6,216,690 B1 | 4/2001 | Keitel et al. |
| 6,571,792 B1 | 6/2003 | Hendrickson et al. |
| 6,745,764 B2 | 6/2004 | Hickle |
| 7,565,905 B2 * | 7/2009 | Hickle .................... 128/203.14 |
| 2003/0065537 A1 | 4/2003 | Evans |
| 2003/0135087 A1 | 7/2003 | Hickle et al. |
| 2003/0154976 A1 | 8/2003 | Dalgetty et al. |
| 2004/0060999 A1 | 4/2004 | Kock |
| 2004/0103897 A1 | 6/2004 | Hickle et al. |
| 2007/0118075 A1 | 5/2007 | Uutela et al. |
| 2007/0149953 A1 | 6/2007 | Tolvanen-Laakso et al. |
| 2008/0097166 A1 | 4/2008 | Yudkovitch et al. |

* cited by examiner

ELECTRONIC ANESTHESIA DELIVERY APPARATUS

CROSS REFERENCES TO RELATED APPLICATIONS

This application is a Continuation-In-Part application claiming priority to and benefit from, currently pending, U.S. patent application Ser. No. 11/031,661, filed on Jan. 7, 2005.

STATEMENT REGARDING FEDERALLY SPONSORED RESEARCH OR DEVELOPMENT

None.

REFERENCE TO SEQUENTIAL LISTINGS, ETC.

None.

BACKGROUND

1. Field of the Invention

The present invention provides an anesthesia delivery apparatus. More specifically, the present invention comprises an electronic anesthesia delivery apparatus for controlling delivery of at least two anesthetic agents from at least two respective diffusers to a patient.

2. Description of the Related Art

Standard anesthesia delivery machines utilize a plurality of mechanical components to deliver a measured amount of anesthesia to a patient, for example, an animal. Many of these standard devices include an oxygen flow meter, a pressure gauge, and a vaporizer. Such vaporizers typically include a canister housing an anesthetic agent and a wicking material. As the wicking material absorbs the anesthetic agent, oxygen flows by the wicking material and vaporizes the anesthetic agent molecules for delivery to the patient. In order to vary the delivery percentage of drug to the user, an oxygen control valve is opened or closed in order to vary the amount of oxygen flowing past the wicking material, thus varying the percentage of drug delivered to the patient. A mechanical thermostat regulates the division of oxygen flow within the vaporizer in order to compensate for changes in temperature of the anesthetic agent due to the vaporizing process, or due to change in room temperature One problem associated with the above mentioned traditional vaporizers is that being mechanical, the vaporizer loses accuracy due to wear of the internal mechanical thermostats and loss of efficiency of the wicking material. Therefore the vaporizer must be periodically removed and sent to a repair facility for overall. Another problem is the specifications for vaporizers on the market today. Most have accuracy of +/−15% of the percentage flow rate indicated and others have accuracy specification of +/−20% of the indicated percentage flow rate of anesthesia. Yet another problem is their up-front expense and the inability to be easily converted to new drug types. In order to convert to a new drug type, the wicking material must be replaced requiring removal of the canister from the machine. Such design is not cost effective. It would be preferable to design a device wherein anesthetic agent may be replaced rather than requiring replacement of the entire canister and the wicking material.

Another weakness of the traditional vaporizers is their percentage of anesthesia output with respect to flow over a time period. Initially the output percentage is low at start up flows and increases to the output dial setting then holds steady at about +/−15 to 20% (percent) of a dial setting through oxygen flows of up to about 7 to 10 liters of flow. After that point the output percentage decreases due to the higher flow-rates of oxygen flowing through the vaporizer.

Another problem is that physicians must manually operate mechanical valves and dials on anesthesia machines. Typically, these valves must be operated at different locations of the anesthesia machine. This is difficult and requires the physician or assistant to look to different locations of the delivery apparatus to make adjustments. Further, the physician or assistant must try to compensate for temperature and flows based on information provided by the gauges. It would be preferable to design a device which may be controlled by a single interface and which compensates for operating conditions electronically.

Given the foregoing, it will be appreciated that an apparatus is required which overcomes the aforementioned difficulties and deficiencies.

SUMMARY OF THE INVENTION

According to one embodiment, an electronic anesthesia delivery apparatus, comprises a chassis having at least one anesthetic vaporizer, an oxygen input port in flow communication with the at least one anesthetic vaporizer, and a touchscreen display mounted to the chassis comprising an electronic touchscreen display for controlling an oxygen flow rate to the at least one anesthetic vaporizer and concentration of anesthetic gas delivered to a patient.

A breathing circuit is defined between a patient and the anesthesia delivery apparatus. The electronic anesthesia delivery apparatus further comprises an oxygen source in fluid communication with the oxygen input port of the anesthesia delivery apparatus. Electronically controlled valves selectively control flow of oxygen from the source to the first and second chambers. A first port is in fluid communication with a first chamber and a second port in fluid communication with a second chamber. An absorber is in fluid communication with a breathing circuit, the absorber scrubbing carbon dioxide from the gas directed therein.

The electronic anesthesia delivery apparatus further comprises an input/output portion having at least one processor in electronic communication with said electronic touchscreen display. The first and second chambers each having a level sensor and a temperature sensor in electronic communication with an input/output portion. The electronically controlled valves are in electronic communication with the input/output portion.

According to a second exemplary embodiment, an electronic anesthesia delivery apparatus comprises a chassis including a first anesthetic agent chamber and a second anesthetic agent chamber, each of the first and second chambers including an anesthetic agent therein. At least one electronically controlled valve is in fluid communication with each of the first agent chamber and the second agent chamber and an oxygen source. The oxygen source is in fluid communication with each of the at least one electronically controlled valves. A touchscreen graphic display having controls corresponding to each of the at least one electronically controlled valves for controlling flow rate and concentration of anesthesia.

The electronic anesthesia delivery apparatus includes at least one electronically controlled valve in electrical communication with an input/output portion and the touchscreen graphic display. The touchscreen graphic display is utilized to start and stop said anesthesia delivery apparatus. The touchscreen graphic display indicates a concentration setting for each of the first anesthetic agent and the second anesthetic agent, as well as an oxygen flow rate through the anesthesia delivery apparatus. The touchscreen graphic display further comprises an agent level indicator for each of the first and second chambers and a plurality of controls and gauges for the electronic anesthesia delivery apparatus. The first and second agent chambers are bubbling diffusers.

According to a third embodiment, an electronic anesthesia delivery apparatus, comprises a chassis comprising first and second anesthetic agent chambers. The first and second agent chambers are in fluid communication with a plurality of electronically controlled valves. A touchscreen graphics display is in electronic communication with the electronically controlled valves. The touchscreen display comprises a plurality of controls for controlling the electronically controlled valves, the touchscreen display further indicating a oxygen flow rate and concentrations of anesthesia. The electronic anesthesia delivery apparatus further comprises an input/output portion in electronic communication with the touchscreen graphic display. The touchscreen graphics display and the electronically controlled valves control concentration and flowrate of at least one anesthesia. The first and second agent chambers comprise bubbling diffusers for mixing oxygen and anesthetic agent. It is also preferable that when a different anesthetic agent is utilized, a chamber which was previously used may be filled with a different anesthetic agent and a processor may be programmed with code containing an algorithm for controlling a concentration.

An electronic anesthesia delivery apparatus for mixing a carrier gas and first and second anesthetic agents comprises a chassis having an electronic vaporizer, the vaporizer having a first anesthetic chamber and a second anesthetic chamber retaining the first anesthetic agent and the second anesthetic agent, a carrier gas input port in flow communication with the first anesthetic chamber and the second anesthetic chamber, a precision orifice and an electronic control valve corresponding to each of the chambers being downstream of the gas input port, each of the chambers having a conduit in flow communication with the carrier gas input port, each of the conduits extending into each of the chambers below an upper level of anesthetic agent, wherein the carrier gas passes through a porous diffuser near an end of the conduit and bubbles through the anesthetic agent, the chamber further comprising an anesthetic gas outlet port, an electronic touchscreen display for controlling carrier gas flow rate to the first anesthetic chamber and the second anesthetic chamber, the electronic touchscreen display further allowing control of concentrations of the anesthetic agent in an anesthesia to a patient by intermittently opening and closing of the electronic control valve, a circuit board having an input/output portion, the circuit board in electronic communication with the electronic touchscreen display, the input/output portion receiving temperature of the anesthetic agent, the electronic anesthesia delivery apparatus allowing use of a first anesthetic agent while a second anesthetic agent is one of either replaced or substituted in the second chamber. The electronic anesthesia delivery apparatus further comprises a carrier gas line which bypasses the first and second anesthetic chambers. The electronic anesthesia delivery apparatus wherein the carrier gas line is in flow communication with the electronic vaporizer downstream of the first and second chambers. The electronic anesthesia delivery apparatus wherein the apparatus allows mixing of two anesthetic agents to be delivered to a patient. The electronic anesthesia delivery apparatus wherein the delivery of the agents occurs independently. The electronic anesthesia delivery apparatus wherein the delivery of the agents occurs simultaneously. The electronic anesthesia delivery apparatus further comprises a flow sensor in flow communication with the carrier gas input port. The electronic anesthesia delivery apparatus wherein the flow sensor senses pressure differentials.

An electronic anesthesia delivery apparatus comprises a chassis having an anesthetic vaporizer including first and second anesthetic chambers and a touchscreen graphics display comprising controls for said anesthetic vaporizer, a circuit board including an input/output portion, the touchscreen graphics display in electronic communications with the circuit board, the circuit board controlling rate of vaporization and concentration of a first and second anesthetic agent disposed in the first and second anesthetic chambers, respectively, at least one electronically controlled valve in fluid communication with each of the first and second anesthetic chambers, the electronically controlled valve in electronic communication with the input/output portion of the circuit board, each of the first anesthetic chamber and the second anesthetic chamber in flow communication with a carrier gas input port, each of the first anesthetic chamber and the second anesthetic chamber having an outlet port, the carrier gas input port in fluid communication with an orifice and the electronically controlled valve, at least one inlet tube in flow communication with the carrier gas input port, each of the at least one inlet tube extending into each of the first and second chambers, wherein either of the first and second anesthetic chambers is refillable while the other of the first and second anesthetic chambers is in use. The electronic anesthesia delivery apparatus further comprises a pulse oximetry sensor in electronic communication with the circuit board. The electronic anesthesia delivery apparatus further comprises an electrocardiography heart wave form. The electronic anesthesia delivery apparatus further comprises a remote control for making operating adjustments. The electronic anesthesia delivery apparatus further comprises an input for a flash memory card. The electronic anesthesia delivery apparatus further comprising a USB port.

An electronic anesthesia delivery apparatus, comprises a chassis having a carrier gas input port, a first anesthetic chamber and a second anesthetic chamber in fluid communication with the carrier gas input port, the first and second anesthetic chambers including an outlet port, a precision orifice and an electronic control valve in fluid communication with the carrier gas input port and the first and second anesthetic chambers, a circuit board including an input/output portion, the electronic control valve in electronic communication with the circuit board, the circuit board controlling the electronic control valve to vary rate of vaporization and concentration of a first anesthetic agent and a second anesthetic agent, a temperature sensor signal in electronic communication with the circuit board, the temperature sensor signal indicating a temperature of the first and second anesthetic agents, a touchscreen graphics display in electronic communication with the circuit board, each anesthetic chamber having a conduit therein and extending to an elevation beneath the anesthetic agent and having at least one diffuser for bubbling carrier gas through the anesthetic agent. The electronic anesthesia delivery apparatus further comprising a carbon dioxide monitor. The electronic anesthesia delivery apparatus further comprising a network connector.

DETAILED DESCRIPTION

Referring now in detail to the drawings, wherein like numerals indicate like elements throughout the several views, there are shown in FIGS. 1-8 various aspects of an electronic anesthesia delivery apparatus which provides several advantages over the prior art. First, the novel electronic anesthesia delivery apparatus utilizes a touchscreen graphics display to electronically control the delivery of anesthesia, or oxygen or other carrier gas alone, to a patient. Second, the device comprises a vaporizer which does not require a wicking material in order to vaporize an anesthetic agent and therefore allows easy conversion from one anesthetic agent to another. Third, the anesthesia delivery apparatus provides improved accuracy in controlling anesthesia output over a range of oxygen flows. For purpose of the following description, anesthesia is meant to comprise an anesthetic agent and a carrier gas such as oxygen, air, nitrous oxide or other suitable carrier. For reasons of clarity of the present description, the carrier gas is stated to be oxygen.

Figure 1:
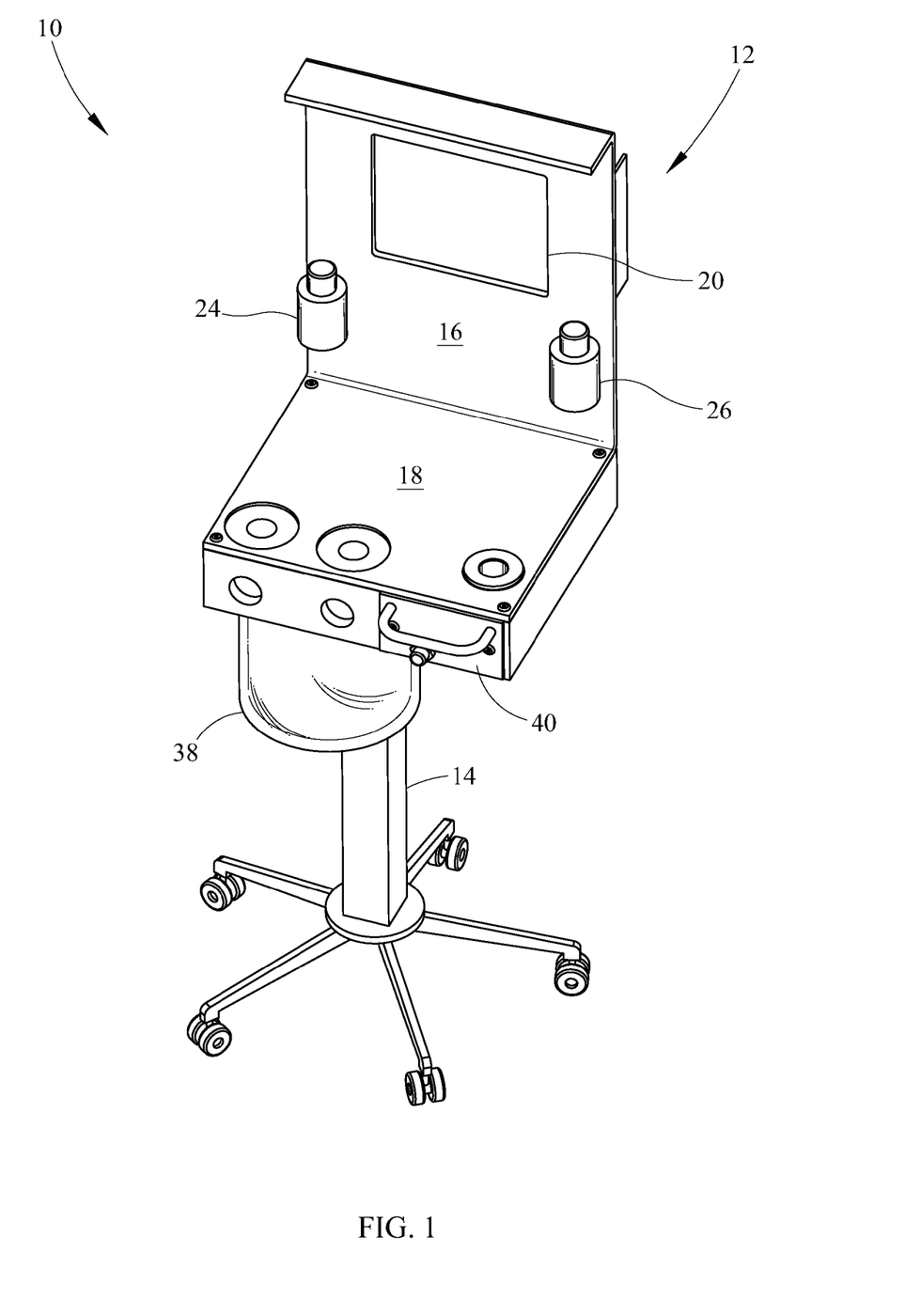
FIG. 1 is a front perspective view of a chassis and stand of an exemplary electronic anesthesia delivery apparatus of the present invention.

Referring initially to FIG. 1, a front perspective view of a chassis for the electronic anesthesia delivery system 10 is depicted. Specifically, the electronic anesthetic delivery apparatus 10 comprises a chassis 12 mounted on a stand 14. As depicted, the stand 14 may comprise a vertical leg and a plurality of rollers mounted at a bottom portion of the vertical leg making the electronic anesthetic delivery apparatus 10 movable between, for example, operating rooms. Alternatively, the stand 14 may comprise a plurality of feet, without wheels, extending from the vertical leg or the chassis 12 may be mounted on a wall in an operating room. The chassis 12 comprises an upper housing 16 and a lower housing 18. The upper housing 16 is substantially rectangular in shape and may further comprise a box-shaped rear cover (not shown). On the front of the upper housing 16 is a window 20 centrally located relative to a vertical axis of the upper housing 16. The window 20 receives a touchscreen graphics display 22 discussed further herein.

Still referring to FIG. 1, extending from the upper housing 16 is at least one anesthetic agent port. The at least one anesthetic agent port is depicted as a first anesthetic agent port 24 and a second anesthetic agent port 26. The first anesthetic agent port 24 is utilized to fill a corresponding first chamber 25 (FIG. 3) with a first type of anesthetic agent for use during the surgical procedure. The first anesthesia port 24 may be color coded or include a sticker of a color corresponding to a first type of anesthetic agent. The second anesthetic agent port 26 is also utilized to fill a corresponding second chamber 27 (FIG. 3) with a corresponding second anesthetic agent which may also be utilized during a surgical procedure. The second anesthetic port 26 may also be color coded or have a color coded sticker which corresponds to the second anesthetic agent utilized for a surgery and to further inhibit use of the wrong anesthetic agent. Each of the first and second ports 24,26 include a cap to open for filling the chambers and to close once the anesthetic chambers 25,27 are filled. In addition, or alternatively, the ports may be keyed mechanically to a specific size or shape, so as to only receive anesthetic agent of a particular type. In such a way, a doctor, nurse or technician cannot fill a port of a particular type with an incorrect agent.

Figure 2:
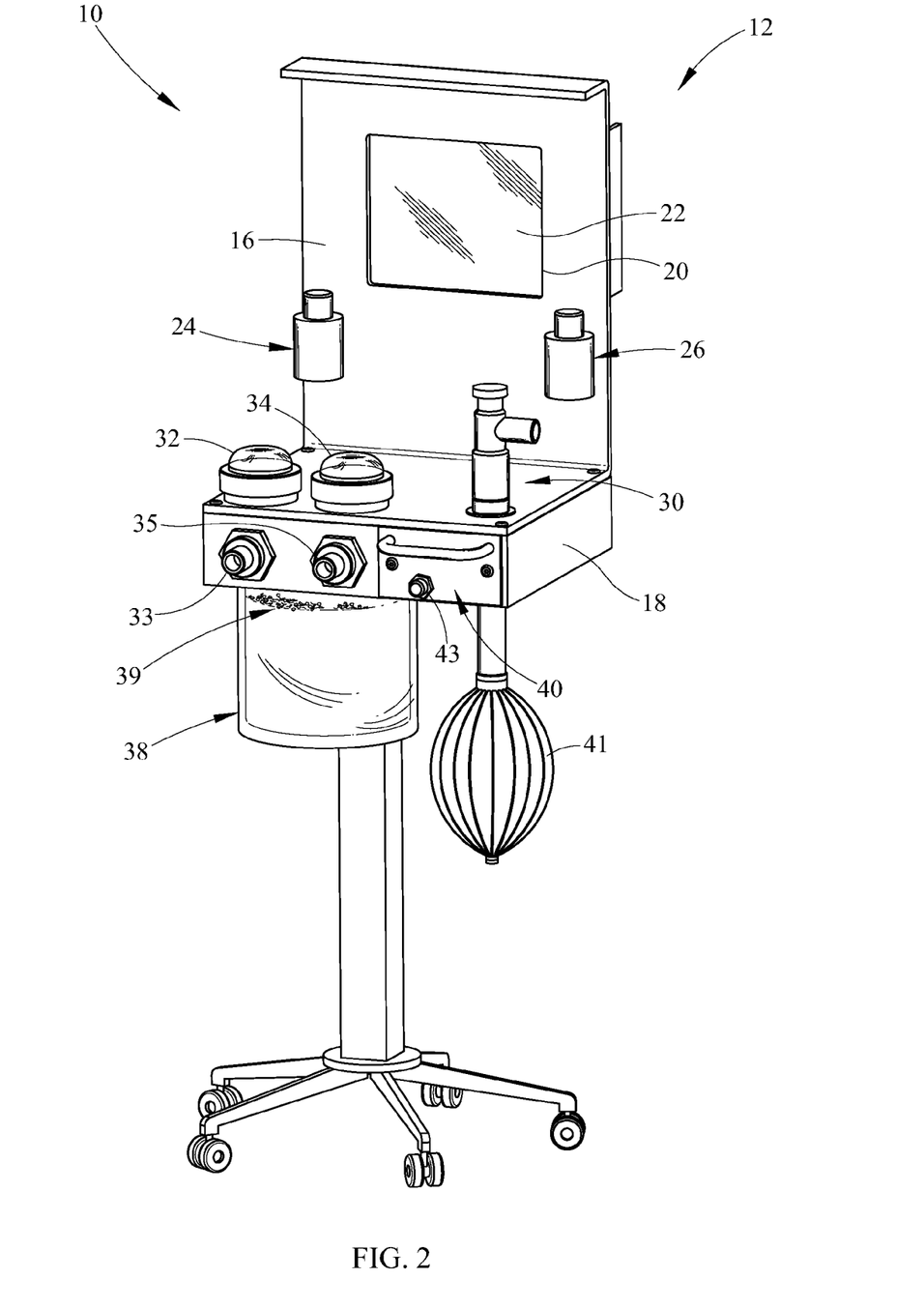
FIG. 2 is a front perspective view of the electronic anesthesia delivery apparatus of FIG. 1 with various operating components attached.

Referring now to FIGS. 1 and 2, the lower housing 18 is substantially rectangular in shape but may comprise alternate shapes. The lower housing 18 also comprises a thickness defining an interior volume wherein a plurality of pipes, tubing, fittings or the like are located in order to partially define a breathing circuit. Alternatively, the lower housing 18 may be formed of a solid block of material wherein ducts defining fluid communication paths may be formed. The lower housing also comprises taps for a pop-off valve 30, an inhalation valve 32 and an exhalation valve 34, each depicted in FIG. 2. The pop-off valve 30 provides a relief or bleed valve bleeding off excess gas and carbon dioxide from the breathing circuit. In fluid communication with the pop-off valve 30 may be a scavenger system (not shown) defined by, for example, either a charcoal filter or a blower and tubing combination. The charcoal filter (not shown) may be utilized to remove anesthetic agent from gas bleeding from the pop-off valve 30 into an interior room of a structure where a surgical procedure is occurring. Alternatively, a blower and tubing combination (not shown) may be connected to the pop-off valve 30. The upstream side of the blower may be in fluid communication with the pop-off valve to receive bleed gas comprising anesthesia and carbon dioxide. Further, the blower may force the anesthesia and carbon dioxide through an exterior wall of the structure wherein the procedure is occurring to atmosphere where the anesthesia diffuses.

As previously indicated an inhalation valve 32 and an exhalation valve 34 are also disposed on the lower housing 18. The inhalation valve 32 may be a check valve which allows flow of anesthesia from the anesthesia delivery apparatus 10 to the patient in only a single direction. The exhalation valve 34 may also be a check valve which allows flow of carbon dioxide and unconsumed anesthesia back to the lower housing 18 for removal of the carbon dioxide, described hereinafter. Also shown on the lower housing 18 is an inhalation port 33 and an exhalation port 35 which connect tubes to the patient. The tubes and ports 33,35 provide fluid communication between the patient and the electronic anesthesia delivery apparatus 10.

The lower housing 18 further comprises a flush valve 40 which provides a high flow rate of oxygen through the anesthesia delivery apparatus 10 and the components therein in order to clear any residual anesthesia in the system from a previous surgical procedure. Further the flush valve 40 may be used to charge a re-breathing bag 41 which is used to manually provide oxygen to a patient. The flush valve 40 is defined by a poppet valve (not shown) within the lower housing 18 which is normally closed but opens when a button 43 on the lower housing 18 is depressed. The exemplary flush valve 40 provides a flow rate of up to about 50 liters per minute depending on the patient, whereas the normal flow rate of oxygen through the anesthesia delivery apparatus 10 may be up to about 4 liters per minute.

Figure 3:
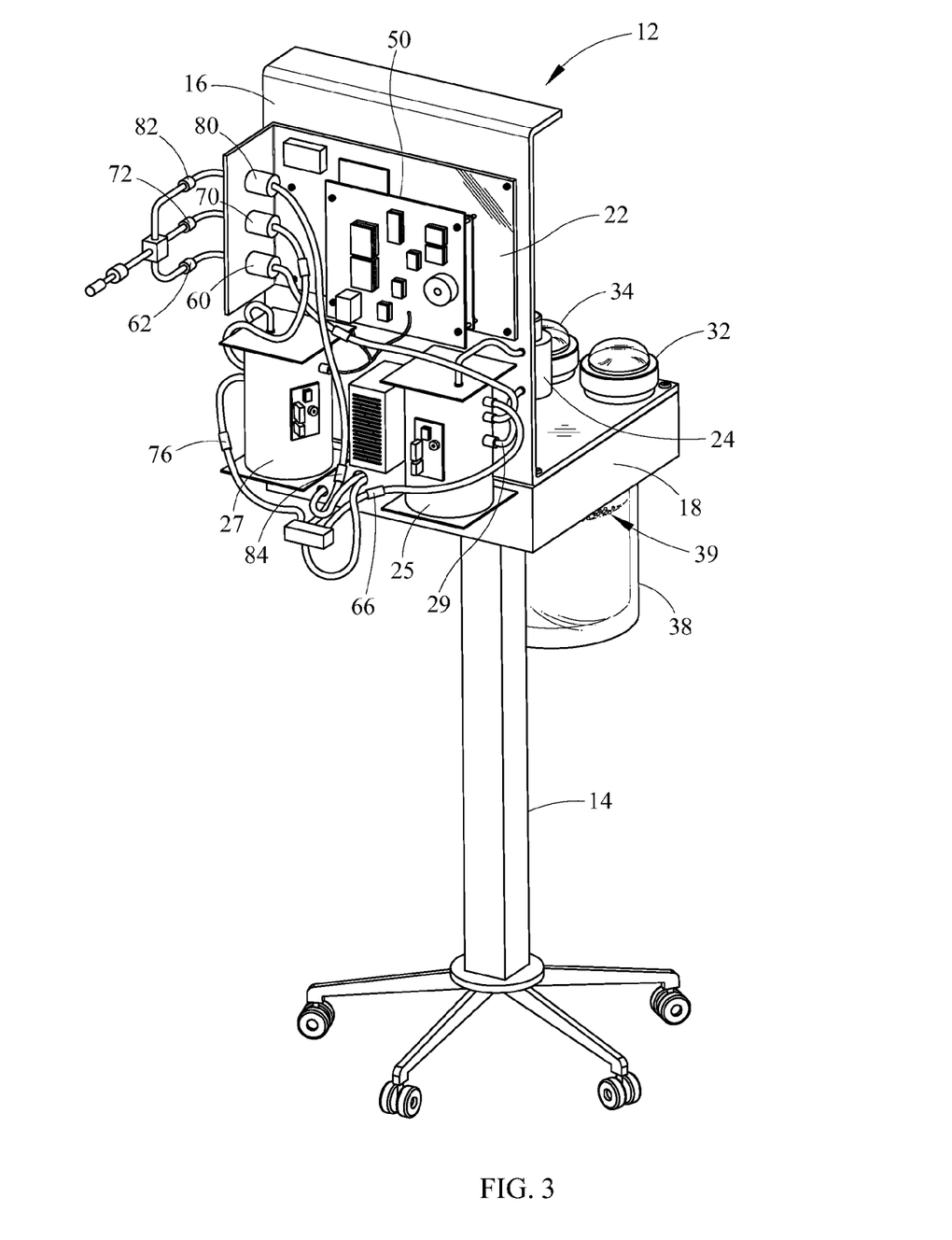
FIG. 3 is a rear perspective view of the electronic anesthesia delivery apparatus of FIG. 2 with the rear cover removed.

Referring now to FIG. 3, a rear perspective view of the anesthesia delivery apparatus 10 is depicted with the rear cover removed. A circuit board 50 is depicted behind the touchscreen graphics display 22. The circuit board 50 comprises an input/output portion 87 (FIG. 6) for communication with controlling and measuring components, memory and at least one processor for running algorithms or programs to regulate concentration of anesthesia. For example the processor may be receiving flow rate and temperature information from the chambers 25,27 and compensating to maintain constant percentage output of anesthesia, thus providing improved control in an electronic manner rather than requiring manual determinations as in the prior art. One advantage of the present device is that the system is upgradeable for new anesthetic agents by upgrading the processor with algorithms corresponding to vaporization of the new drug. Also located on the rear surface of the upper housing 16 are first and second chambers 25, 27 corresponding to the first anesthesia port 24 and second anesthesia port 26, respectively. A fill pipe 29 provides fluid communication between the first anesthesia port 24 and the first chamber 25. A second fill pipe (not shown) also extends between the second anesthesia port 26 and the second chamber 27. The first and second chambers 25,27 are sealed pressure vessels substantially cylindrical in shape with a hollow interior defining a storage area for anesthetic agent and vaporization of the anesthetic agent. The chambers 25,27 further comprise ports which receive oxygen input from a pressurized source. The ports may be located at the bottoms of the chambers 25,27 in order to best diffuse the anesthetic agent therein. During operation the oxygen diffuses through the chambers 25,27 vaporizing the anesthetic agent and forming a vaporized anesthetic agent which is combined with an oxygen flow to define an anesthesia of a preselected concentration. According to the present invention the concentrations may be adjusted electronically with the touchscreen graphics display 22. Moreover, the circuit board 50 may comprise on-board memory which stores algorithms corresponding to various anesthetic agents. If a new agent is used, a corresponding algorithm should be programmed for accurate vaporization of the new anesthetic agent.

Also depicted in FIGS. 1-3, is an absorber 38. The absorber 38 is in fluid communication with the exhaled gas of the patient which contains both carbon dioxide and unconsumed anesthesia. The carbon dioxide is absorbed by a plurality of pellets 39 contained within the absorber canister 38. The pellets 39 may be formed of sodalime material, which is commercially known as Sodasorb and comprises hydrated lime and sodium hydroxide. After the carbon dioxide is removed or scrubbed, the unconsumed anesthesia is directed to the inhalation breathing circuit for delivery to the patient.

Figure 4:
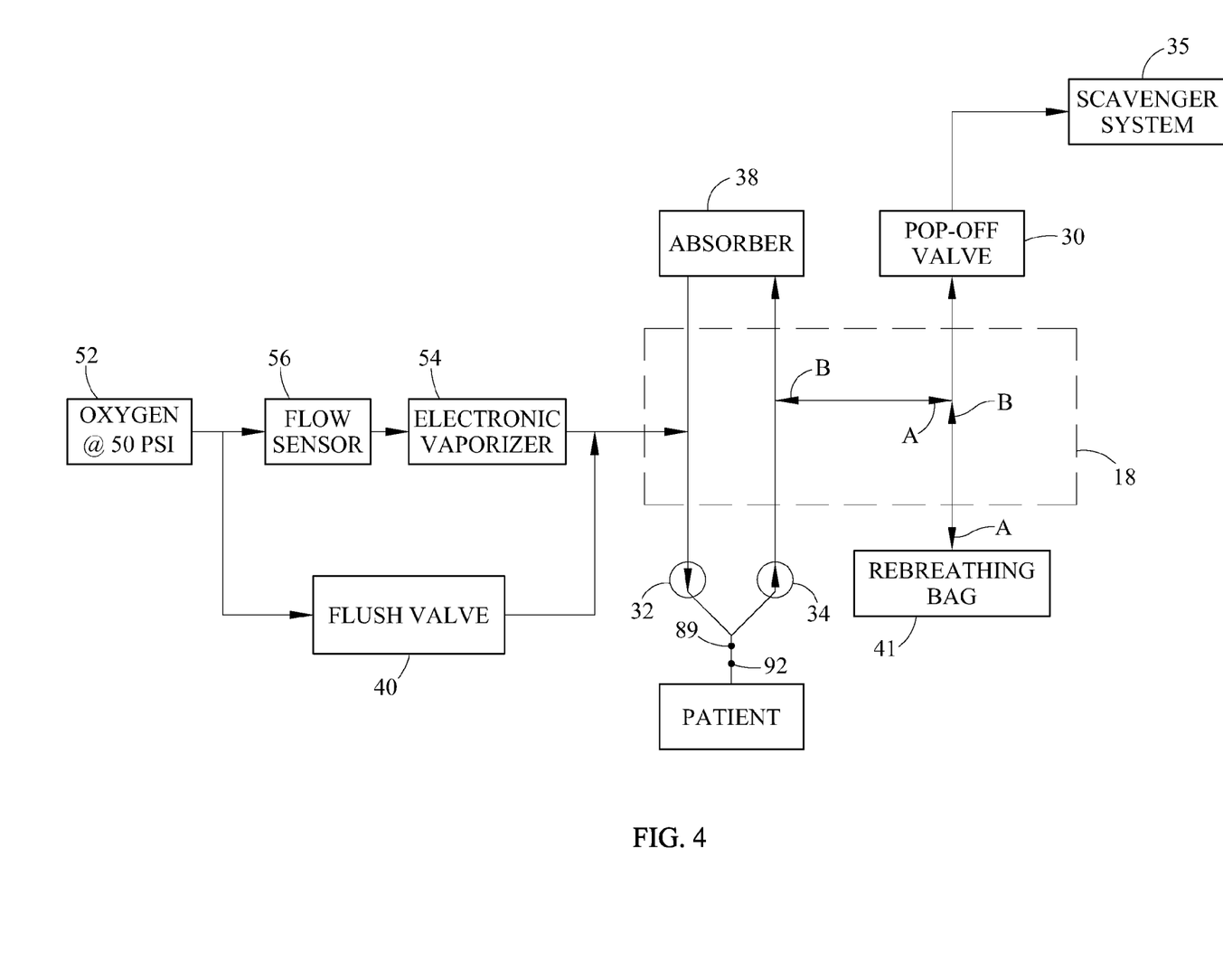
FIG. 4 is a schematic diagram of the electronic anesthesia delivery apparatus of FIG. 2.

Referring now to FIG. 4, a schematic diagram of the anesthesia delivery apparatus 10 is depicted which generally indicates the flow paths of the electronic anesthesia delivery apparatus 10. The schematic diagram depicts an oxygen source 52 in fluid communication with a flow sensor 56 and an electronic vaporizer 54. The flow sensor 56 detects flow of oxygen to the apparatus 10 by comprising a thermistor which detects temperature changes. For example, when pressurized oxygen flows over the thermistor, the thermistor senses a temperature drop due to the cooler temperature of the pressurized oxygen. However, when the flow stops, the thermistor provides a normal temperature signal which indicates that the pressurized oxygen has stopped flowing. By way of example, the flow sensor 56 may alternatively be a pressure sensor to detect flow of oxygen to the apparatus 10 by comprising a transducer which detects pressure changes. For example, the flow of pressurized oxygen causes a differential pressure to arise. However, when the flow stops, the transducer provides a zero-pressure differential signal. As described further herein, various electronically controlled valves are utilized to control the flow of oxygen between preselected ranges, for example between 0 and 4 liters per minute for delivery to the electronic vaporizer 54. As described further herein, the electronic vaporizer 54 comprises the first chamber 25 and the second chamber 27 which allow vaporization of anesthetic agent by the oxygen supplied by the oxygen source 52 creating a vaporized anesthetic agent which, in turn, is mixed with oxygen to form anesthesia. Adjacent the vaporizer 54 and flow sensor 56 is the flush valve 40 which is arranged in a bypass configuration so that the oxygen from the oxygen source 52 does not pass through the vaporizer 54 and the flow sensor 56 before charging the remaining portions of the anesthesia delivery apparatus 10. As previously indicated the flush valve 40 is used to charge and clear residual anesthesia or diffused anesthetic agent remaining within the anesthesia delivery apparatus 10.

Referring still to FIG. 4, once the oxygen passes through the electronic vaporizer 54 and flow sensor 56 the resultant anesthesia enters the lower housing 18, shown in broken lines, which comprises a plurality of tubing, piping, fittings or the like for delivery to and from the patient as well as ducting between a lower housing and the absorber 38 and pop-off valve 30. This movement of anesthesia to and from the patient defines a breathing circuit between the anesthetic delivery apparatus 10 and the patient. Specifically, the anesthesia enters the lower housing 18 and moves through a duct to the patient which the patient inhales through the inhalation check valve 32 (FIG. 3). When the patient exhales, the exhaled gas comprising carbon dioxide and unconsumed anesthesia passes through the exhalation valve 34. As indicated in the schematic, the exhaled gas moves in the direction indicated by arrows "A" through ducting in the lower housing 18 to a re-breathing bag 41 (FIG. 2) which depends from a stem beneath the pop-off valve 30 FIG. 2. The re-breathing bag 41 captures exhaled gas and further may be manually depressed by a doctor during the surgical procedure on the patient in order to provide a breath to the patient. During exhalation, the re-breathing bag 41 becomes filled at which time remaining exhaled gas or air is directed to the pop-off valve 30 and on to the scavenging system 35. During a subsequent inhalation by the patient, the gas within the re-breathing bag 41 is pulled to the absorber 38 indicated by arrow B where remaining carbon dioxide is scrubbed. The figure depicts two lines extending between the absorber 38 and the re-breathing bag 41 for ease of description and understanding. However, it is well within the scope of the present invention that a single line may be utilized with two-way flow therein between the absorber 38 and the re-breathing bag 41. Further, it should be understood by one of ordinary skill in the art that piping may be positioned outside the lower housing 18 and still extend between the indicated components.

Once inside the absorber 38, the carbon dioxide is scrubbed utilizing the plurality of pellets 39 to remove carbon dioxide from the exhaled gas. The remaining anesthesia is directed from the absorber 38 into the lower housing 18 to the patient for inhalation with the incoming anesthesia from the vaporizer 54. Such a system is commonly referred to as a rebreathing system which decreases the amount of wasted anesthesia and is therefore a more efficient system for use in administering anesthesia during a surgical procedure. However, it is well within the scope of the present invention that the dual anesthetic chamber and touchscreen design may be utilized without the rebreathing circuit. For instance, in anesthetizing small animals like guinea pigs or mice a physician may choose not to utilize the rebreathing system because of the large volumes of gas stored in the system as compared to the small respiratory volume of the animal. Such large volumes vary the response time of changes to anesthesia flow which should be precise with such small patients. Thus it should be understood that the anesthesia delivery apparatus may allow for bypass of the rebreathing circuit.

Also in fluid communication with the lower housing is the pop-off or bleed valve 30 which continually bleeds off exhaled anesthesia. During a surgical procedure gas is continually being added to the breathing circuit. In order to inhibit pressure build-up, some gas must be bled from the system. Thus, the bleed valve 30 is utilized. Since the rebreathing bag 41 fills before gas is directed to the bleed valve 30, the bleed valve 30 receives the last portions of exhaled gases from the patient's lungs. Accordingly, this gas comprises higher concentrations of carbon dioxide since it is usually the last of the exhaled gases from the lungs. This also makes the system more efficient because the absorber 38 is scrubbing less carbon dioxide and therefore the scrubbing pellets 39 last longer. As previously indicated the pop-off or bleed valve 30 may be connected to a scavenger system 35 which includes either or both of a charcoal filter to scrub anesthesia from the gas being relieved at the pop-off valve 30 or a blower and tubing assembly in order to direct anesthesia from within the interior structure of a building to outside the structure for diffusion to atmosphere.

Figure 5:
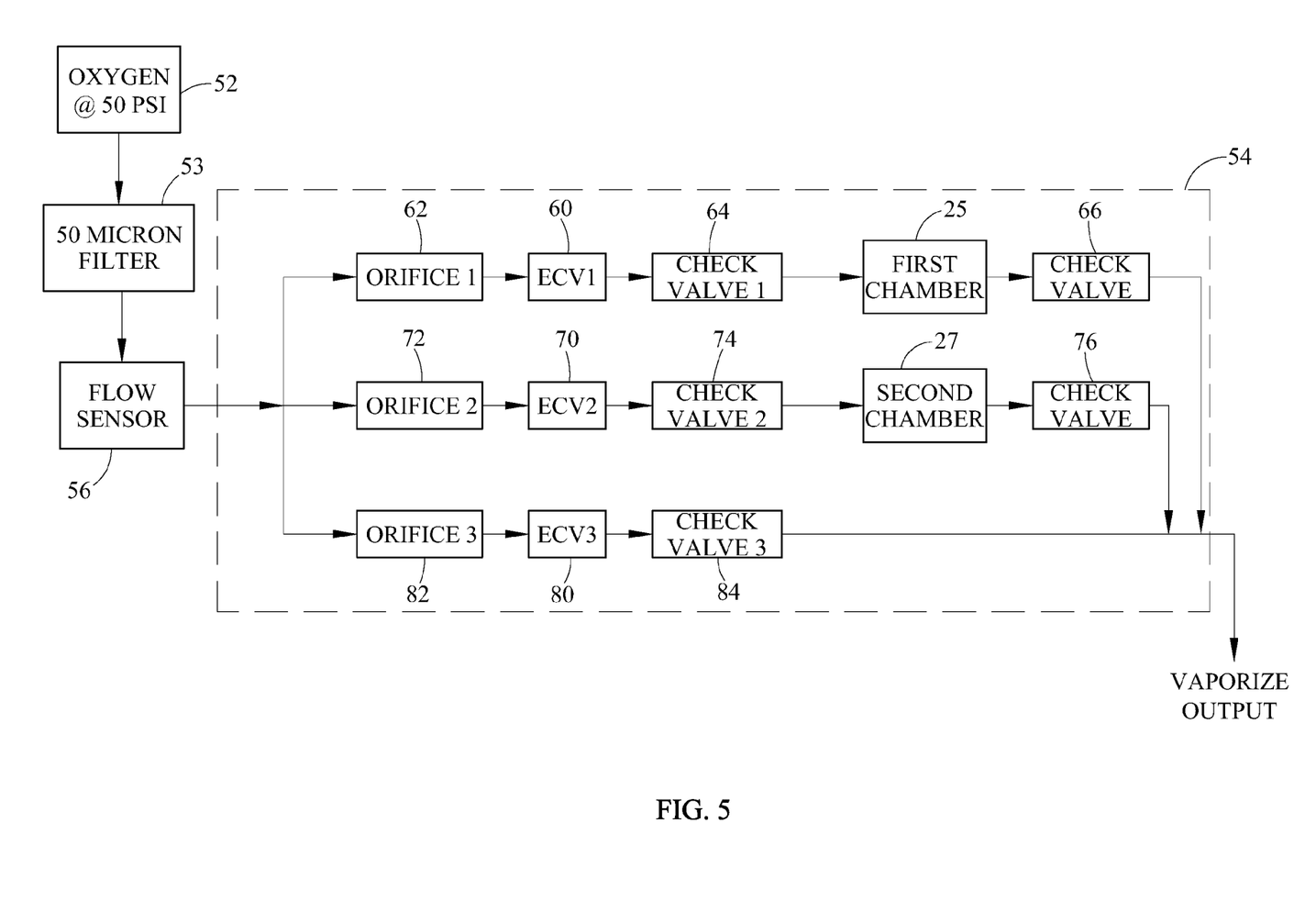
FIG. 5 is a schematic diagram of the vaporizer utilized with the electronic anesthesia delivery apparatus of FIG. 2.
Figure 8:
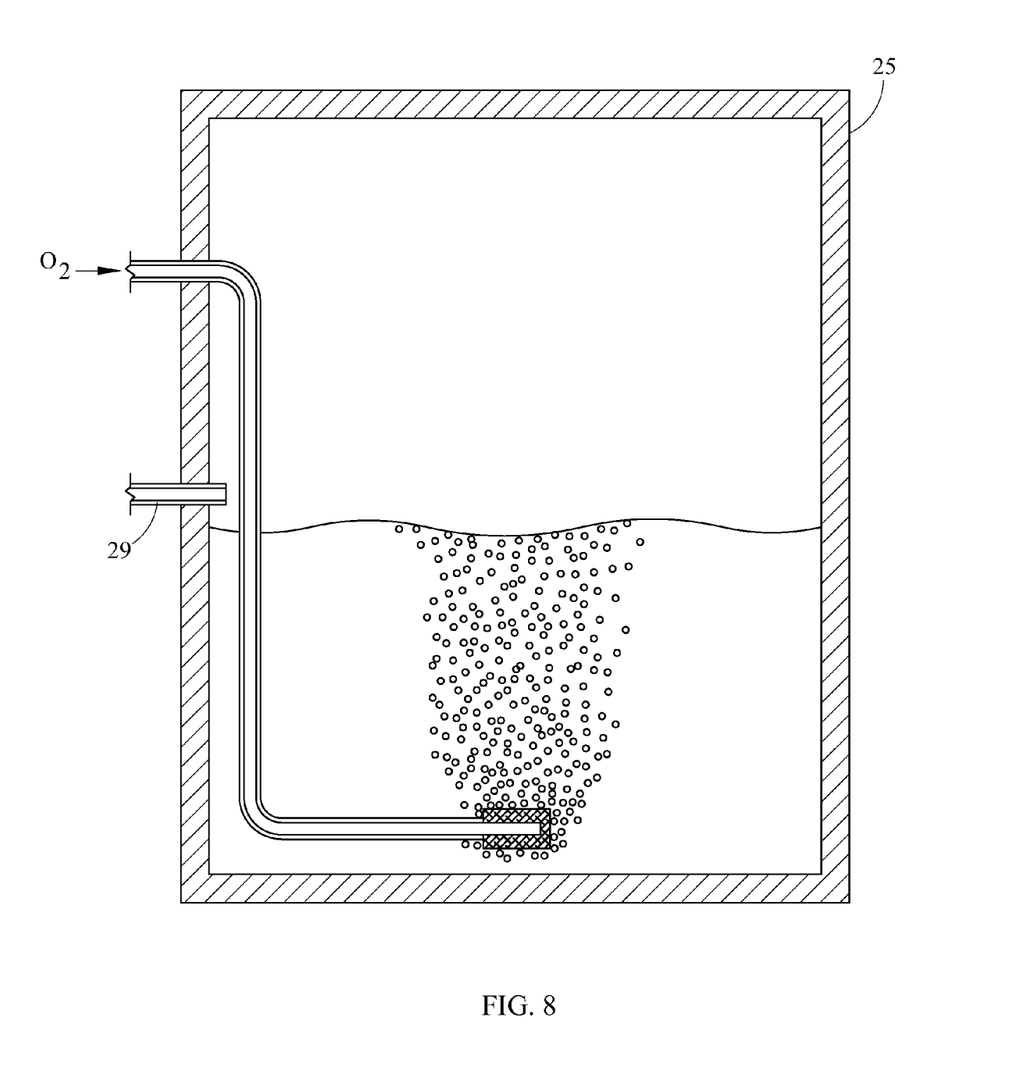

Referring now to FIG. 5, a block diagram is shown indicating flow of oxygen through the electronic vaporizer 54 indicated by the broken line. Initially oxygen from the oxygen source 52 may pass through a filter 53 to remove any impurities over a preselected size, for example, fifty microns, before moving to the flow sensor 56. Upon leaving the flow sensor 56 the oxygen enters the electronic vaporizer 54 which comprises three possible paths for the oxygen. According to the first path wherein the oxygen diffuses and vaporizes the first anesthetic agent in the first chamber 25, the oxygen first flows through a precision orifice 62 and then through an electronically controlled valve 60 which is in electronic communication with the circuit board 50. The orifice 62 is sized according to vaporization requirements of the first anesthetic agent. Vaporization depends on the type of agent, the temperature of the agent, and the volume of flow into the agent. The precision orifice 62 allows regulation of the volume of flow by providing a baseline for making adjustments and controlling concentrations. As indicated the touchscreen graphics display 22 may be utilized to open or close the valve 60 through a selected amount of time as indicated and selected on the display 22 in order to control the concentration of anesthetic agent. Accordingly, a solenoid or the like may provide for movement of the valve 60. After passing through the precision orifice 62 the oxygen flows through a first check valve 64 which allows one directional flow to the first agent chamber 25. Alternatively stated, the first check valve 64 prevents anesthetic agent from moving upstream from the electronic vaporizer 54. As depicted in FIG. 8, once in the first chamber 25, the oxygen moves through a tube to a porous diffusing portion which allows the oxygen to diffuse through the anesthetic agent in a bubble form causing vaporization. As the bubbles diffuse in the first anesthetic agent, for example isoflurane, and exit the chamber 25 carrying molecules of anesthetic agent, a vaporized anesthetic agent is produced. The vaporized anesthetic agent is then directed through a check valve 66 to mix with oxygen and form the anesthesia at the selected concentration. The check valve 66 inhibits anesthesia to flow backward to the chamber 25. By utilizing the touchscreen graphics display 22, the first chamber electronic valve 60 selectively controls oxygen flow causing either intermittent or continual flow to the chamber 25 depending on the settings input on the graphics display 22. During this time, oxygen also flows through an electronic valve 80, a precision orifice 82, and a check valve 84. The pipe in fluid communication with the valve 80, orifice 82, and check valve 84 is also in fluid communication with the pipes comprising the first chamber 25 and the second chamber 27 and therefore defines an output for the vaporizer 54. The electronic valve 80 is in electrical communication with the graphics display 22 in order to open and close the valve 80 and provide a desired flow rate of oxygen. The valve 80 may include a solenoid to provide opening and closing of valve 80. The diffused anesthetic agent from the first chamber 25 and the oxygen mix before exiting the electronic vaporizer 54 and define an anesthesia of a preselected concentration measured as percent anesthetic agent by volume of total oxygen flow.

According to a second flow path, the oxygen may flow through a second electronically controlled valve 70 in order to pass through the second chamber 27. Like the first electronic valve 60, the second electronically controlled valve 70 is in electrical communication with the circuit board 50 and therefore may be controlled by the touchscreen graphics display 22. Such control also allows the valve 70 to be opened or closed according to the concentration of anesthesia required during the surgical procedure. Once the electronically controlled valve 70 is opened the oxygen passes through the precision orifice 72 and to the valve 70. As previously indicated, the precision orifice 72 is sized according to the dimensions required for vaporization of the anesthetic agent. After passing through the valve 70 the oxygen then passes to the second chamber 27. The second chamber 27 may include, for instance, sevoflurane which may commonly be utilized with isoflurane during a surgical procedure. After the oxygen bubbles through the second chamber 27 and is diffused in order to produce a diffused anesthetic agent, the diffused agent passes through a check valve 76 and mixes with oxygen passing through valve 80 to form an anesthesia. The check valve 76 also inhibits back flow to the second chamber 27. The anesthesia passes from the electronic vaporizer 54 at a preselected concentration measured as percent by volume and indicated on the graphics display 22. Alternatively, both the first valve 60 and the second valve 70 are opened in order to allow diffused anesthetic agent to be produced from both the first chamber 25 and the second chamber 27. Such configuration is desirable when both chambers comprise the same anesthetic agent or if two agents need to be mixed for use during a surgical procedure.

According to a third possible flow path, pure oxygen may be administered to a patient prior to a surgical procedure to saturate the patient's body with oxygen. According to an alternate scenario, the pure oxygen may be administered following the surgical procedure in order to bring the patient out from the anesthetic effects. In order to provide pure oxygen to a patient, the electronically controlled valves 60,70 are closed and the electronically controlled valve 80 is opened to a selected flow rate, as indicated on the graphics display 22. In fluid communication with the electronically controlled valve 80 is an orifice 82 and a check valve 84 which all direct flow from the oxygen source to the lower housing 18 and on to the patient. As shown in FIG. 5, by closing valves 60, 70 and opening valve 80, only oxygen is output from the vaporizer 54. It should be understood that the various signals sent to the electronically controlled valves 60,70, 80 may be part of feedback control loops in order to control the dynamic behavior of the system. In addition, such a feedback control loop allows better accuracy in maintaining constant output percentage of anesthesia.

Figure 6:
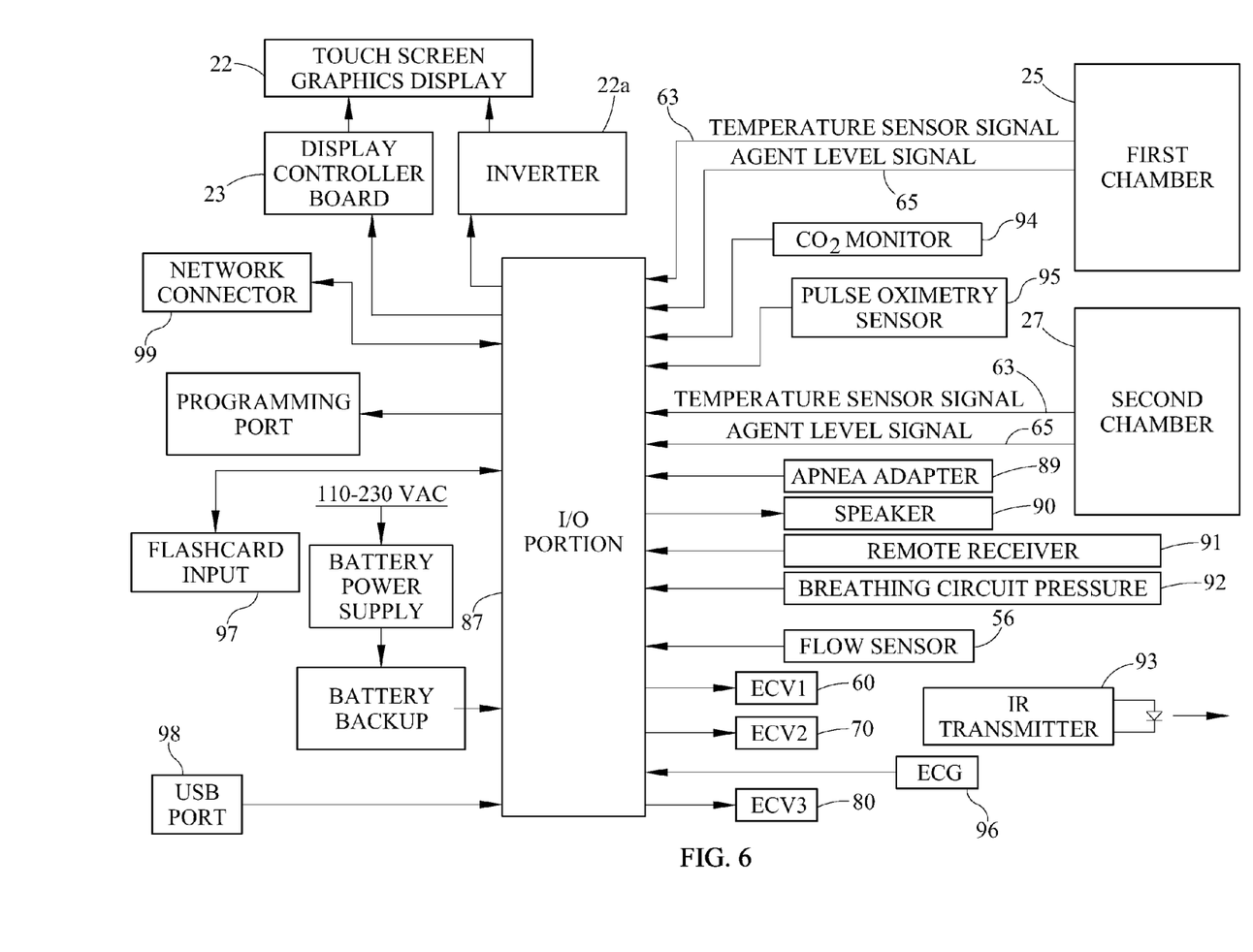
FIG. 6 is an electrical block diagram of the electronic anesthesia delivery apparatus of FIG. 2.

Referring now to FIG. 6, an electrical block diagram generally indicates the various electrical connections utilized in the electronic anesthesia delivery apparatus 10. The circuit board 50 (FIG. 3) comprises an input/output (I/O) portion 87 comprising a plurality of inputs and outputs with various components of the electronic anesthesia delivery apparatus 10. The I/O portion 87 of the circuit board 50 provides a signal to an inverter 22a which operates a back light (not shown) for the touchscreen graphics display 22. Specifically the inverter 22a steps up the 5 volt DC signal to a several hundred volts in order to illuminate a backlight for the graphics display 22. The I/O portion 87 also provides a signal to a display controller board 23 based on signals input from various other measuring and signal components in communication with the I/O portion 87. The display controller board 23 comprises a video card and flash memory to produce the graphical user-interface which indicates the operating conditions and parameters, however various components may be utilized to produce graphical user-interface on the graphics display 22. The signal received from the I/O portion 87 is graphically produced on the display 22 by the display controller board 23.

The first and second chambers 25,27 comprise sensors which are in electrical communication with the I/O portion 87. The first chamber 25 and the second chamber 27 each comprise a temperature sensor (not shown) which sends a temperature signal 63 to the I/O portion 87. The temperature sensor measures the agent temperature and is important because the anesthetic agent changes temperature during vaporization. This temperature change affects further vaporization and must be compensated for. Such compensation is made by algorithms on the circuit board 50 for instance by a processor or microprocessor. Accordingly, a temperature measurement must be made.

In addition to the temperature signals delivered to the I/O portion 87, an agent level signal 65 is also delivered from the first and second chambers 25,27. As described further, the touchscreen graphics display 22 indicates the amount of anesthetic agent in each of the first and second chambers 25,27. According to one embodiment a capacitance sensor may be utilized to provide a signal to the I/O portion 87. With the agent level signal 65 received from the capacitance sensors the levels of the chambers 25,27 are visually indicated on the display 22. This prevents running out of anesthetic agent during a surgical procedure.

The I/O portion 87 also receives a signal from an apnea adapter 89 which comprises a thermistor positioned in the breathing passageway of the patient. The adapter 89 sends a signal based on temperature differences measured when the patient breathes. For example, the temperature will raise during exhalation and will drop during inhalation. If the I/O portion 87 fails to receive a signal from the apnea adapter 89 within a preselected time period, the processor concludes that the patient is not breathing properly and an alarm may sound from a speaker 90.

The I/O portion 87 may also receive a signal from a remote infrared receiver 91. The electronic anesthesia delivery apparatus 10 may also comprise a remote control or transmitter 93 which sends an infrared signal to the remote infrared receiver 91 which in turn communicates with the I/O portion 87. The remote control 93 may communicate with the receiver 91 to increase or decrease oxygen flow rates by controlling valve 80 or increase or decrease flow rates of oxygen through the first and second chambers 25,27 thereby controlling rates of vaporization and therefore concentrations of anesthetic agent in anesthesia.

The I/O portion 87 also receives a signal from a breathing circuit pressure sensor 92. The breathing circuit pressure sensor 92 is also measured at the breathing passageway of the patient and is utilized to measure the breathing pressure of the circuit so as not to harm the patient and further to insure enough pressure is present to deliver anesthesia to the patient. If the breathing circuit pressure falls outside a preselected range the signal may cause an alarm which notifies a physician through the speaker 90.

The I/O portion 87 also receives a signal from the flow sensor 56 indicating flow of oxygen into the electronic vaporizer 52. If the flow sensor 56 sends a signal that flow is not available, an alarm may sound through the speaker 90 indicating to a user that the condition should be corrected.

The apparatus also comprises AC or DC power capability. The device may receive AC power from 110 or 230 volt source. Alternatively, the device may be operated from a DC battery power supply. In addition to these power sources, the device 10 may further comprise a battery backup in an AC power supply is lost during a surgical procedure.

Figure 7:
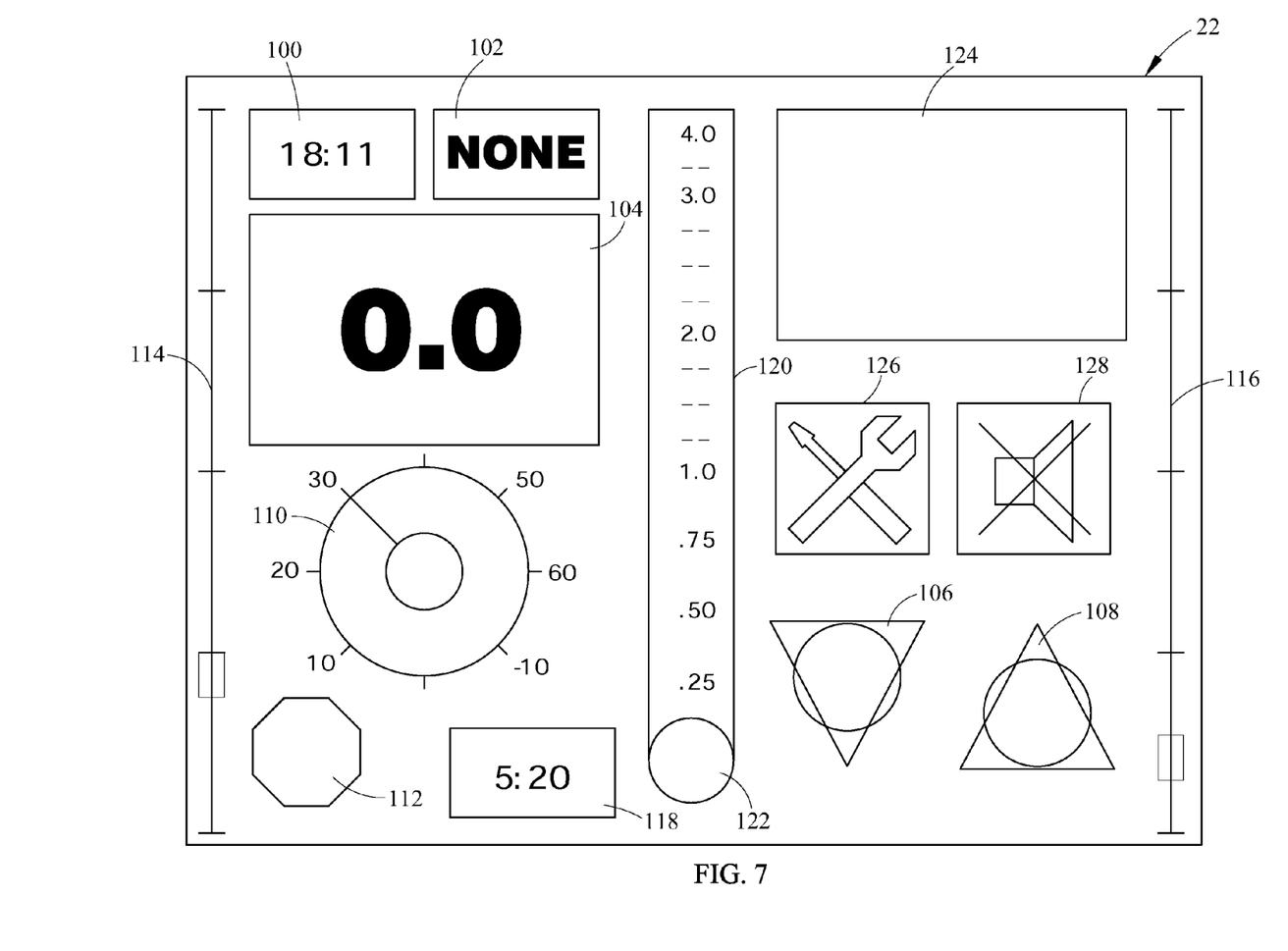
FIG. 7 is a front view of an exemplary touchscreen graphic display utilized with the present invention; and, FIG. 8 is a side sectional view of an exemplary anesthetic agent chamber depicting the diffusion process.

Referring now to FIG. 7, a front view of the touchscreen graphics display 22 is shown which comprises the graphical users interface. The interface depicted on the display 22 allows the user to control various components of the electronic anesthesia delivery apparatus 10. At the upper left hand corner of the display 22 is a real time clock 100 which may display 12-hour time or 24-hour time as depicted. Adjacent the real time clock 100 is an agent identification (ID) window 102 which indicates "None". By pressing the agent ID window 102 and the up/down toggles 106, 108, the agent ID toggles through the selections "None", the first anesthetic agent, for example "Isoflurane", and the second anesthetic agent, for example "Sevoflurane". The window 102 may also change color according to the corresponding color code for the drug indicated. When the first anesthetic agent is displayed in the agent ID window 102, the toggles 106,108 are utilized to control concentrations of that anesthetic agent. Alternatively, when the second anesthetic agent is highlighted in the agent ID window 102 the toggles 106,108 are utilized control changes to the second anesthetic agent. Thus, the toggles 106, 108 control movement of the electronic control valves 60,70 thus varying the concentration of the diffused anesthetic agent. By pressing the agent ID button 102 again, the ID returns to "None" as depicted. Thus the user presses the agent ID window 102 and toggles through the selections until the desired agent may be controlled.

Beneath the clock 100 and the agent ID 102 is a virtual concentration setting 104 which depicts a percent by volume of an agent which is highlighted in the agent ID window 102. For example, when the first anesthetic agent is highlighted in the agent ID window 102, the concentration of the first anesthetic agent is shown in the concentration setting 104. The same condition occurs when the second anesthetic agent is highlighted in the agent ID window 102. When a desired agent is selected, the corresponding concentration setting 104 may be adjusted for that anesthetic agent. The concentration being output for each anesthetic agent 104 is measured in percent of anesthetic agent by volume and may range, for example, up to about 10 percent.

Beneath the concentration setting 104 is a digital pressure gauge 110 which records pressure within the breathing system. For example, the digital gauge may be a virtual analog gauge and as depicted, the digital gauge 110 is circular in shape with a digital needle indicating the pressure within the breathing system. The digital pressure gauge 110 receives a signal via the I/O portion 87 from the breathing circuit pressure sensor 92 (FIG. 6). As previously indicated, the breathing circuit pressure sensor 92 (FIG. 4) is located as close to the patient as possible to obtain accurate readings of pressure at the patient. The gauge 110 is shown indicating pressure in centimeters of water.

Along the left hand side of the touchscreen graphics display 22 is a virtual first level indicator 114 for the first anesthetic agent in the first chamber 25. The first level indicator 114 receives a signal via the I/O portion 87 from the agent level signal 65 (FIG. 6). By indicating the level of agent in the first chamber 25, the user knows when a refill of anesthetic agent is necessary prior to starting a procedure. This is particularly useful so that a chamber does not empty during a procedure which would require refilling and could harm the patient. On the right hand side of the touchscreen display 22 is a virtual second level indicator 116 which indicates the level of second anesthetic agent in the second chamber 27. The first and second level indicators 114,116 may both include bars indicating agent levels or may include virtual moving indicators which move along a level bar as depicted.

Beneath the pressure gauge 110 is an octagonal shape which indicates a stop button 112 for the anesthesia delivery apparatus 10. The stop button 112 is pressed when a procedure is finished and the anesthesia delivery is no longer needed. The stop button 112 may be colored red on the display 22 which is commonly recognized as a stop signal. Also beneath the breathing pressure gauge 110 is a case clock 118 which may be used by a physician to bill for time on a particular surgical procedure or to bill for amount of anesthesia utilized. The case clock 118 may be stopped by pressing the stop button 112, thus marking the time of the surgical procedure.

In the middle of the touchscreen display 22 is a virtual oxygen flow meter which receives a signal from a flowmeter and indicates the total flow of oxygen being delivered from the electronic vaporizer 54. Alternatively, the electronic control valve 80 may cycle on and off and utilizing known cycle rates with an algorithm, the oxygen flow rate may be ascertained and displayed. Although various flow rates may be utilized, the present exemplary embodiment comprises a design which delivers up to 4 liters of oxygen per minute. At a lowermost position of the oxygen flowmeter 120 is a start button 122 which starts oxygen flow to the patient to begin a procedure. The start button 122 may be colored green to indicate a start function to a user. Once the button 122 is depressed, the oxygen flow may be increased using toggle button 108 or decreased using toggle button 106 as will be indicated on the flowmeter 120. The toggle buttons 106,108 are therefore controlling the electronic control valve 80 in order to vary the oxygen flow through the system.

Also shown on the touchscreen graphics display 22 is an alarm or warning screen 124. The alarm screen 124 provides a visual indication to a user that an alarm condition has been triggered. For instance, the apnea adapter or sensor 89 may be triggered by a lack of breath from the patient after a preselected amount of time, or the flow sensor 56 may cause an alarm if oxygen from the source 52 is not flowing. Thus, in addition to the audible alarm signal provided by the speaker 90, the alarm screen 124 may provide a visual indication of an alarm condition which should be corrected.

Beneath the alarm screen 124 is a configuration button 126 which allows a user to configure various settings, alarm conditions and the like. Adjacent the configuration button 126 is an mute or override button 128 which silences the audible alarm for a preselected period of time. For example, if an alarm sounds a user may press the override button 128 which cancels the audible alarm from speaker 90 for an adjustable time period of, for example, 2 minutes. This muted time period is also a period which may be set utilizing the configuration button 126. After, the two minute period, if the alarm condition is not corrected, the alarm will sound again.

Alternatively to the touchscreen graphical display 22, a plurality of devices may be utilized. For instance, a graphics screen such as an LCD or CRT monitor may be used in combination with a separate touchpad or keypad programmed for use with the anesthesia device. Further, a trackball or mouse-type pointing device may be utilized with the display to make selections and adjustments to the system. Accordingly, such embodiments should be understood to be within the scope of the present disclosure.

As further alternatives, the anesthesia delivery apparatus 10 may include a carbon dioxide ($CO_2$) sensor or monitor 94 to measure $CO_2$ levels and so that the apnea sensor will not be needed or may be replaced. Additionally, a pulse oximetry sensor 95 may be utilized for measuring oxygen levels in the patient. Such sensor 95 is in electronic communication with the circuit board and may be output on the graphic display screen. Further, electrocardiogram (ECG) sensor 96 may be added to the apparatus 10 so that heart wave forms may be provided from the apparatus. The ECG measuring device 96 is also in electronic communication with the circuit board, and further comprises electrodes in electronic communication with the circuit board which are used to receive data and produce the electrocardiogram. Even further, a remote control 93 functionality may be utilized with the touchscreen or display which allows for movement of a cursor or selector about the screen and may include at least one button to make selections shown in the screen. As a further alternative, an input 97 for a flashcard may be provided to allow for flash re-programming or additional programming for new or different anesthetic agents. The flashcard and input would be in communication with the circuit board and input/output portion of the apparatus 10. As a further option or alternative to this input, a USB port 98 may be utilized instead of or in addition to the flashcard input so as to allow connection to a computer or other device and allow for the previously described additional programming or re-programming of code related to algorithms for the various anesthetic agents which are available now or may be available in the future. Such USB port would also be in communication with the input/output portion 87 and the circuit board to allow for remote-troubleshooting or also allow downloading of surgical related data from use of the apparatus 10. Additionally a network connector 99, wired or wireless, may also be used to connect the apparatus 10 for troubleshooting or updates. Standards for connectivity will be known to one skilled in the art.

In operation a carrier gas source, for example a 50 psi oxygen source, is connected to an inlet port. The anesthesia delivery apparatus 10 is connected to an A/C power source and powered on. Initially, various electronics and components of the apparatus 10 will go through a self-test to verify proper function. The alarm screen 124 will display the progress of this test and pass/fail information will be posted. If any component fails the unit will be put in permanent failsafe mode or for some non-critical test the user can continue by pressing an override mode key (not shown) or key combination. Alternatively, when the self-test is successfully completed the apparatus 10 will go into ready status waiting on user input.

Next the physician or an assistant can connect their external disposable breathing hoses to the patient and the ports 33,35. The physician next touches the virtual oxygen flow control start button 122 at which time the virtual flowmeter 120 will become highlighted or illuminated indicating the microprocessor is ready for increments or decrements to set the flowrate. The physician increases the flow to a desired setting by pressing the up toggle 108. Next the apparatus begins immediately delivering oxygen upon selection of an oxygen flow greater than 0. The case clock 118 begins timing when the oxygen flow begins.

Once the correct oxygen flow is achieved the user then touches the anesthetic agent selection box 102. This will highlight. The physician would then press the up or down arrows to cycle through the selections of the first anesthetic agent, for example isoflurane, the second anesthetic agent, for example sevoflurane, and the none selection. Other drugs or drugs developed in the future may be programmed into the system. Once the desired anesthetic agent is displayed, the physician touches the concentration setting window 104 to select the output concentration of agent desired. The window 104 will highlight and the physician uses the toggles 106,108 to select the percentage of agent. Next the anesthesia begins delivery upon choosing a percentage greater than 0.

During operation the virtual pressure gauge 110 displays the patient lung pressures being realized. Sensors monitor these pressures as well as breath detections, agent percentage settings and many other safety related parameters. If any of the sensors detect an unsafe condition, an alarm may sound. At any time the physician can adjust the carrier gas flow settings or by pressing the stop button 112 on the display 22 can cease all flows and stop the case clock. By pressing the stop button 112 the delivery apparatus 10 "ends the case" and is put into standby mode. By pressing anywhere on the display 22 the unit can be re-activated and ready for input. The override or mute virtual button 128 may be pressed to silence the alarms for 2 minutes. Further, alarm conditions are displayed on the alarm screen 124. The unit is intended to be left on and go into a sleep mode however, the physician or an assistant may turn off and on each day if they desire.

The foregoing description of several methods and an embodiment of the invention have been presented for purposes of illustration. It is not intended to be exhaustive or to limit the invention to the precise steps and/or forms disclosed, and obviously many modifications and variations are possible in light of the above teaching. It is intended that the scope of the invention be defined by the claims appended hereto.

What is claimed is:

1. An electronic anesthesia delivery apparatus for mixing a carrier gas and first and second anesthetic agents comprising:
   a chassis having an electronic vaporizer, said vaporizer having a first anesthetic chamber retaining said first anesthetic agent and a second anesthetic chamber retaining said second anesthetic agent;
   a carrier gas input port in flow communication with said first anesthetic chamber and said second anesthetic chamber, a precision orifice and an electronic control valve corresponding to each of said chambers being downstream of said gas input port, each of said chambers having a conduit in flow communication with said carrier gas input port, each of said conduits extending into each of said chambers below an upper level of anesthetic agent, wherein said carrier gas passes through a porous diffuser near an end of said conduit and bubbles through said anesthetic agent;
   said chamber further comprising an anesthetic gas outlet port;
   an electronic touchscreen display for controlling carrier gas flow rate to said first anesthetic chamber and said second anesthetic chamber, said electronic touchscreen display further allowing control of concentrations of said anesthetic agent in an anesthesia to a patient by intermittently opening and closing of said electronic control valve;
   a circuit board having an input/output portion, said circuit board in electronic communication with said electronic touchscreen display, said input/output portion receiving temperature of said anesthetic agent;
   said electronic anesthesia delivery apparatus allowing use of a first anesthetic agent while a second anesthetic agent is one of either replaced or substituted in said second chamber.

2. The electronic anesthesia delivery apparatus of claim 1 further comprising a carrier gas line which bypasses said first and second anesthetic chambers.

3. The electronic anesthesia delivery apparatus of claim 2, said carrier gas line in flow communication with said electronic vaporizer downstream of said first and second chambers.

4. The electronic anesthesia delivery apparatus of claim 1 wherein said apparatus allows delivery of said anesthetic agents to said patient.

5. The electronic anesthesia delivery apparatus of claim 4 wherein said delivery of said agents occurs independently.

6. The electronic anesthesia delivery apparatus of claim 4 wherein said delivery of said agents occurs simultaneously.

7. The electronic anesthesia delivery apparatus of claim 1 further comprising a flow sensor in flow communication with said carrier gas input port.

8. The electronic anesthesia delivery apparatus of claim 7 said flow sensor sensing pressure differentials.

9. An electronic anesthesia delivery apparatus, comprising:
   a chassis having an anesthetic vaporizer including first and second anesthetic chambers and a touchscreen graphics display comprising controls for said anesthetic vaporizer;
   a circuit board including an input/output portion, said touchscreen graphics display in electronic communications with said circuit board, said circuit board controlling rate of vaporization and concentration of a first and second anesthetic agent disposed in said first and second anesthetic chambers, respectively;
   at least one electronically controlled valve in fluid communication with each of said first and second anesthetic chambers, said electronically controlled valve in electronic communication with said input/output portion of said circuit board;
   each of said first anesthetic chamber and said second anesthetic chamber in flow communication with a carrier gas input port, each of said first anesthetic chamber and said second anesthetic chamber having an outlet port;
   said carrier gas input port in fluid communication with an orifice and said electronically controlled valve;
   at least one inlet tube in flow communication with said carrier gas input port, each of said at least one inlet tube extending into each of said first and second chambers;
   wherein either of said first and second anesthetic chambers is refillable while the other of said first and second anesthetic chambers is in use.

10. The electronic anesthesia delivery apparatus of claim 9 further comprising a pulse oximetry sensor in electronic communication with said circuit board.

11. The electronic anesthesia delivery apparatus of claim 9 further comprising an electrocardiogram heart wave form.

12. The electronic anesthesia delivery apparatus of claim 9 further comprising a remote control for making operating adjustments.

13. The electronic anesthesia delivery apparatus of claim 9 further comprising an input for a flash memory card.

14. The electronic anesthesia delivery apparatus of claim 9 further comprising a USB port.

15. An electronic anesthesia delivery apparatus, comprising:
- a chassis having a carrier gas input port;
- a first anesthetic chamber and a second anesthetic chamber in fluid communication with said carrier gas input port, said first and second anesthetic chambers including an outlet port;
- a precision orifice and an electronic control valve in fluid communication with said carrier gas input port and said first and second anesthetic chambers;
- a circuit board including an input/output portion, said electronic control valve in electronic communication with said circuit board, said circuit board controlling said electronic control valve to vary rate of vaporization and concentration of a first anesthetic agent and a second anesthetic agent;
- a temperature sensor signal in electronic communication with said circuit board, said temperature sensor signal indicating a temperature of said first anesthetic agent and said second anesthetic agent;
- a touchscreen graphics display in electronic communication with said circuit board;
- each anesthetic chamber having a conduit therein and extending to an elevation beneath said anesthetic agent and having at least one diffuser for bubbling carrier gas through said anesthetic agent.

16. The electronic anesthesia delivery apparatus of claim 15 further comprising a carbon dioxide monitor.

17. The electronic anesthesia delivery apparatus of claim 15 further comprising a network connector.

18. The electronic anesthesia delivery apparatus of claim 1 further comprising a carbon dioxide monitor.

19. The electronic anesthesia delivery apparatus of claim 9 further comprising a carbon dioxide monitor.

* * * * *